March 30, 1937. C. F. BERTANZEL, SR Plant Pat. 240
ROSE
Filed Oct. 12. 1936
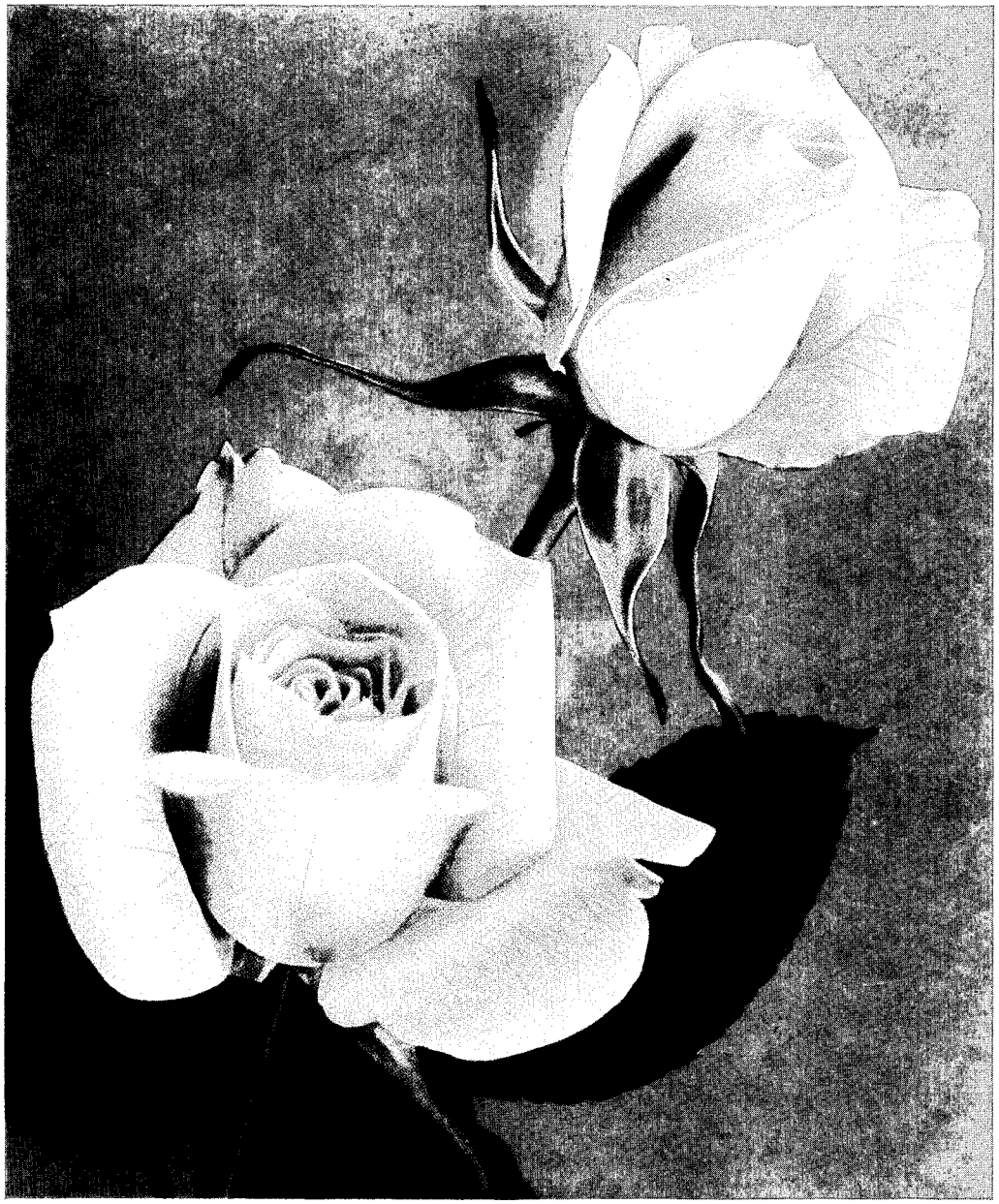
Inventor
C. F. Bertanzel, Sr.
deceased.
By C. F. Bertanzel Jr. and
Harry W. Moore, executors.
By Robb & Robb
Attorneys Patented Mar. 30, 1937

UNITED STATES PATENT OFFICE

240

ROSE

Carl F. Bertanzel, Sr., deceased, late of Roslyn, N. Y., by Carl F. Bertanzel, Jr., Roslyn, N. Y., and Harry W. Moore, Mineola, N. Y., executors, assignors to Carl F. Bertanzel, Jr., Roslyn, N. Y.

Application October 12, 1936, Serial No. 105,348

1 Claim. (Cl. 47—61)

The present discovery relates to a new and distinct rose plant originating as a sport of the well known variety "Talisman."

In the development of this new rose, the inventor found that it is characterized as to novelty as regards its parent by its greater productivity and size of bloom, but its principal feature is that it is very double—a high centered double sport, entirely distinct from anything known to him, having particular regard to its deep shade of gold in the combination of characters above mentioned.

Asexual reproduction of this new variety shows the characteristics herein set forth to be fixed.

The following is a detailed description of this new rose, references to color being in accordance with the Gravereaux color standard:—

Parentage:

Sport of Talisman.

Classification:

Botanic and commercial—Hybrid tea.

*Flower*

Blooming habit:

Recurrent—Continuous.

Other habit—Better production than Talisman.

Bud:

*Size.*—Large.

*Form.*—Pointed, unaffected by wet or hot weather.

*Color.*—When sepals first divide—saffron; when petals begin to unfurl—saffron; when half blown—gold.

*Sepals.*—Smooth edge, "hood" above bud; curl back when bud half open.

*Calyx.*—Shape—funnel. Size—broad. Aspect—smooth. Odor when rubbed—none.

*Peduncle.*—Length—very long. Aspect—smooth. Color—medium green. Strength—erect, heavy.

*Opening.*—Opens well and is unaffected by adverse conditions.

Bloom:

*Size.*—Large, average size when fully expanded 3½ to 4 inches.

*Borne.*—Singly.

*Stems.*—Long, strong.

*Form.*—When first open, high center. Permanence, outer petals curl back.

*Petalage.*—Double (full but open center). Number of petals under normal conditions—35 to 40.

*Color.*—Center of flower—gold. Outer petals—gold. Base of petals (aiglet)—saffron. Inside of petals—gold. Reverse of petals—gold. General tonality from a distance—gold.

*Variegations.*—None.

*Discoloration.*—General tonality at end of first and second days, gold. At end of third day, straw.

Petals:

*Texture.*—Thick; unaffected by wet or hot weather.

*Appearance.*—Inside satiny; outside shiny.

*Form.*—Round.

*Arrangement.*—Imbricated (regularly arranged shinglelike). Petaloids in center, few, small.

*Persistence.*—Drop off cleanly.

*Fragrance.*—Slight. Nature—tea (average hybrid tea scent).

*Lasting quality.*—On the plant and as cut flower very long.

Genital organs:

*Stamens, anthers.*—Large, many. Color—yellow. Arrangement—regular around styles.

*Stamens, filaments (threads).*—Medium. Color—yellow.

*Pollen.*—Lemon yellow.

*Styles.*—Loosely separated, uneven length. Medium, long. Heavy.

*Stigmas.*—White.

*Ovaries.*—All enclosed in calyx.

Fruit:

Variety is fertile with its own pollen.

*Form.*—Ovoid, round headed.

*Aspect.*—Smooth.

*Color at maturity.*—Orange.

*Sepals.*—Caducous (soon falling).

*Plant*

Form:

Bush.

Growth:

Very vigorous.

Foliage:

Five, sometimes seven, leaflets.

*Size.*—Very large.

*Quantity.*—Abundant.

*Color.*—New foliage—light green with bronzy tints. Old foliage—upper side, normal green. Under side, lighter.

*Shape.*—Lanceolate.

*Texture.*—Upper side glossy. Under side smooth. Ribs and veins prominent.

*Edge.*—Serrated (saw toothed).

*Serrations.*—Single, large.

*Rachis.*—Color green. Underside—prickles.

*Stipules.*—Medium, smooth.

*Disease resistance.*—Resistant.

Wood:

*New wood.* — Color — light green. Bark — smooth.

*Old wood.*—Color—green. Bark—smooth.

Thorns: (Divided into thorns, prickles, and short needles.)

*Thorns.*—Quantity—on main stalks from base, ordinary on laterals from stalk, few. Form—broad base, long and medium. Hooked downward. Color when young—green and red. Position—irregular.

*Prickles and short needles.*—None.

From the foregoing it will be noted that the main distinguishing characteristics, either considered separately or in combination, are as follows:

1. Highly productive quality.
2. Large size, high center and doubleness of blooms.
3. Deep shade of gold color of flowers.

What is claimed is:

A new and distinct variety of rose plant characterized as to novelty by its highly productive quality, and the high centered double character and deep gold shade of its bloom, substantially as shown and described.

CARL F. BERTANZEL, JR.,
HARRY W. MOORE,
*Executors of the Estate of Carl F. Bertanzel, Sr., Deceased.*